United States Patent [19]

Luo

[11] Patent Number: 5,439,573

[45] Date of Patent: Aug. 8, 1995

[54] CONCENTRATING ELECTROELUTINON APPARATUS

[76] Inventor: Xiao-Zhong Luo, 625 Brister St. #11, Memphis, Tenn. 38111

[21] Appl. No.: 180,343

[22] Filed: Jan. 12, 1994

[51] Int. Cl.$^6$ .................... G01N 27/26; G01N 27/447
[52] U.S. Cl. ........................... 204/182.8; 204/180.1; 204/182.3; 204/299 R; 204/301
[58] Field of Search ................ 204/182.8, 299 R, 301, 204/182.3, 182.6, 180.1

[56] References Cited

U.S. PATENT DOCUMENTS

| | | | |
|---|---|---|---|
| 4,159,933 | 7/1979 | Allington et al. | 204/299 R |
| 4,545,888 | 10/1985 | Walsh | 204/301 |
| 4,725,348 | 2/1988 | Diekmann | 204/299 R |
| 4,750,982 | 6/1988 | Tomblin et al. | 204/299 R |
| 4,863,582 | 9/1989 | Wijangco et al. | 204/299 R |
| 4,964,961 | 10/1990 | Brautigam et al. | 204/299 R X |
| 5,102,518 | 4/1992 | Doering et al. | 204/180.1 |

OTHER PUBLICATIONS

*Recombinant DNA Techniques: An Introduction*, Rodriguez and Tait, 1983, Pub: Benjamin/Cummings pp. 67–79.

Gaastra and Jorgensen "The Extraction and Isolation of DNA from Gles", *Methods in Molecular Biology*, vol. 2, 1984, Humana Press, pp. 67–76.

*Current Protocols in Molecular Biology*, 1993, Ausbel, et al, ed., pp. 2.0.5–2.0.6, 2.6.1–2.6.2, and 10.5.1–10.5.2.

"Gel Electrophoresis of DNA", *Molecular Cloning*, Sambrook et al., eds., 1989, pp. 6.2–6.23 and 6.28–6.29.

Hansen et al., "Rapid and Simple Purification of PCR Products by Direct Band Elution During Agarose Gel Electrophoresis", *Biotechniques*, vol. 14, No. 1, 1993, pp. 28–29.

Zhen, et al., "A Simple and High Yield Method for Recovering DNA from Agarose Gels", Biotechniques vol. 14, No. 6, 1993, pp. 894–898.

*Primary Examiner*—John Niebling
*Assistant Examiner*—John S. Starsiak, Jr.
*Attorney, Agent, or Firm*—Richard C. Litman

[57] ABSTRACT

An electrophoretic gel elutor and concentrator includes a semi-permeable collecting membrane having a continuously diminishing cross-section terminating in an apex, and a supporting frame of matching configuration. This apparatus is useful in electrophoretic extraction of biological samples which have been previously cut from a separation gel. The apparatus is used with standard electrophoresis equipment including a buffer tank, electrodes, and a power source. Due to the high effective cross-section of the collecting membrane, electrophoretic elution can be carried out quickly and efficiently. Due to the continuously diminishing cross-section to the apex of the collecting membrane, the biological sample is advantageously concentrated and extractions of 99% theoretical yield from a separated gel fragment is possible.

9 Claims, 3 Drawing Sheets

FIG. I

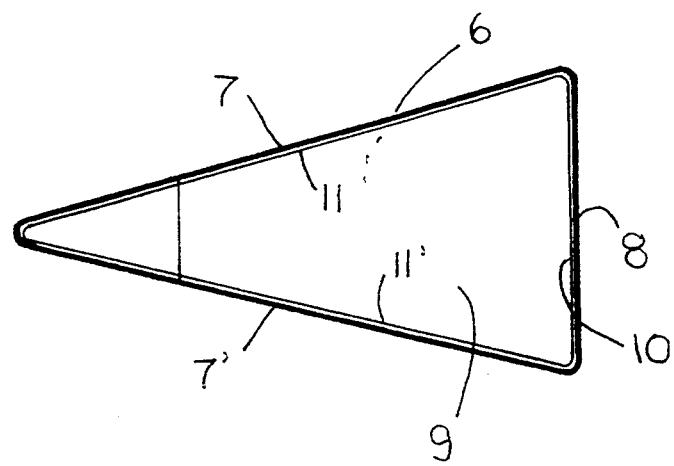
FIG. 2
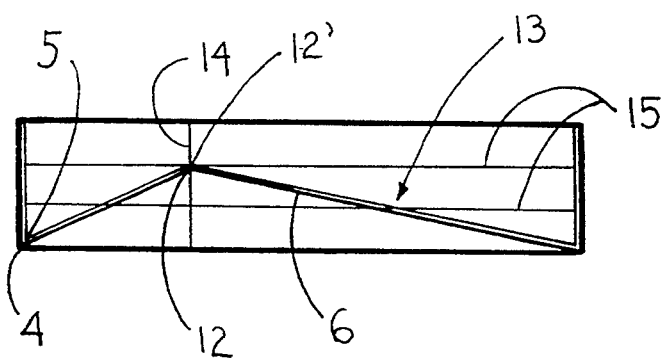
FIG. 3
FIG. 4
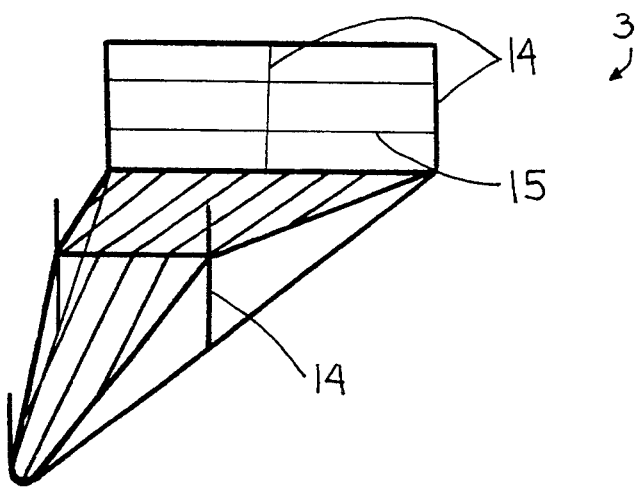

CONCENTRATING ELECTROELUTINON APPARATUS

BACKGROUND OF THE INVENTION

1. Field of the Invention

The present invention relates to an apparatus and methods for the purification and/or isolation of biological samples. More specifically, the present invention relates to an apparatus and methods for electrically eluting and concentrating biological samples such as DNA or proteins separated on electrophoresis gels.

2. Description of the Prior Art

The use of gel electrophoresis to separate a heterogeneous mixture into constituent molecules is an effective and widely accepted method for assaying and/or analyzing biological samples. Nucleic acids, proteins, and other constituent biomolecules migrate in an unidirectional or bidirectional electrical field to bands or spots along a gel according to their electrophoretic properties. These properties include 1) charge, 2) molecular weight, and 3) structural configuration. Typically, these bands or spots are prepared for visualization using dyes applied to the gel after separation. Alternatively, markers or labels may be tagged to the constituent molecules of interest before separation. An overview of procedures for gel electrophoretic separation is given in *RECOMBINANT DNA TECHNIQUES: AN INTRODUCTION*, by Rodriguez and Tait, 1983 Benjamin/Cummings Pub., pp 67–79. Though a powerful tool for analysis, gel electrophoresis has up to now been of limited utility in the extraction of separated molecules due to the difficulty in removing the molecules from the gel in a pure concentrate. Various methods and devices are known for extracting nucleic acids and proteins from gel medium.

Wim Gaastra and Per Lina Jorgensen, "The Extraction and Isolation of DNA from Gels," *Methods in Molecular Biology*, vol. 2, 1984 Humana Press, pp 67–76, discuss standard protocols presently practiced in the art for extraction from gels. Of particular interest is the discussion of electroelution methods (Methods 1 and 2, pp. 69–71). Though these methods are disclosed to have the advantage of producing the highest yields of sample eluted from gels, electroelution procedures generally have disadvantages such as high expense, difficult handling, and/or loss of sample from dilution.

Other advantages and concomitant disadvantages of current techniques in electroelution of biological samples from gels are discussed in *Current Protocols in Molecular Biology*, 1993, Ausubel et al., editors, pp. 2.0.5–2.0.6, 2.6.1–2.6.2, and 10.5.1–10.5.2, as well as in "Gel Electrophoresis of DNA," *Molecular Cloning*, 1989, Sambrook et al., editors, pp. 6.2–6.23 and 6.28–6.29. From these discussions, it can be seen that the dialysis bag type electroelution method, with all its noted disadvantages, remains a standard practice.

In efforts to overcome some of the deficiencies in these standard protocols, modifications have been proposed, both in terms of procedural steps and in specialized equipment. For example, H. Hansen, et al. "Rapid and Simple Purification of PCR Products by Direct Band Elution During Agarose Gel Electrophoresis," *BioTechniques*, 1993, pp. 28–29 discloses a modification of the trough method of electroelution. Therein troughs or trap slots are cut in an agarose separation gel, without the placement of DEAE-cellulose paper or a dialysis membrane in the trap slot. Submarine electrophoresis is run in a unit with a UV-transparent bottom, for monitoring the band migration. Before the band of interest reaches the trap slot, the slot is filled with buffer, preferably of reduced pH to slow and focus the electrophoresis. Once the band containing the biological sample of interest has eluted into the trap slot, electrophoresis is halted, and the sample is removed from the trough with a micropipet. This method requires careful monitoring, as well as time-critical application and replenishment of a special buffer. Further, various considerations, such as the distance between loading and trap slots, UV illumination frequencies, and the like, require highly subjective yet critical decisions. Also, there is some loss of sample due to incomplete elution from the gel, reentrance of sample into the gel below the trap slot, and/or other physical limitations when the gel is not isolated from the collection area.

Zhen et al. in "A Simple and High Yield Method for Recovering DNA from Agarose Gels," *Biotechniques*, 1993, pp 894–898, disclose another trough elution method, wherein a band containing DNA of interest is cut from a preparatory separation gel, and placed in the cut trough of another gel, along with a polyethylene glycol (PEG) modified buffer. Electrophoresis is run until the DNA elutes out of the cut band and into the trough. The DNA is then pipetted into a microcentrifugation tube. The PEG additive must then be removed by extraction. This method suffers from the same limitations as the method of Hansen et al.

Various electroelution devices have been the subject of earlier patents. For example, U.S. Pat. No. 4,545,888 to Walsh discloses an electrophoresis device for the recovery of nucleic acids and other substances wherein large charged molecules are recovered from a separation gel to a binding cellulose resin through a plurality of transfer chambers. The use of the binding resin in this patent requires a further elution step, leading to loss of sample during transfer and elution.

U.S. Pat. Nos. 4,750,982 to Tomblin et al. and 4,863,582 to Wijanco et al. disclose devices for purifying and concentrating DNA onto a dialysis membrane. Though these devices include various segments of decreasing diameter, the dialysis membrane at the plane of contact with samples is flat. These devices are usually quite complicated, space consuming, and use duplicate elements already necessary for preparatory electrophoretic separation. Processes for using these devices are complicated and time consuming, leading to low recovery efficiency. Further, there is no sample concentrating effect during elution.

U.S. Pat. No. 4,964,961 to Brautigam et al. discloses devices useful for electroelution which feature a tapered tube, and a separable collection cup having a circular planar collection membrane. There is loss of sample when employing the device of Brautigam. Again, samples are not concentrated during elution. Similarly, U.S. Pat. No. 5,102,518 to Doering et al. discloses an electroelution device designed for use with epindorf centrifugation tubes. Bubble formation at the bottom of the collecting tube and the complicated processing procedures required decrease the recovery efficiency when employing this device.

None of the above inventions and patents, taken either singly or in combination, is seen to describe the instant invention as claimed.

SUMMARY OF THE INVENTION

The present invention is an electrophoretic gel eluting and sample concentrating apparatus that includes a semi-permeable collecting membrane having a continuously diminishing cross-section terminating in an apex supported by a correspondingly configured open frame. The principle of the present invention lies in that, unlike the known prior art implementations, the present invention requires that the semi-permeable membrane itself, and not just a non-permeable support structure, narrows in cross-section to substantially a point or apex.

The continuously diminishing cross-sectional configuration of the present collecting semi-permeable membrane advantageously facilitates the extraction and concentration of biological samples, such as DNA fragments or proteins that have been previously separated by gel electrophoresis, with improved concentrated yields. The recovery efficiency of electroelution for a membrane is proportional to the highest cross-sectional area of the membrane perpendicular to the electrical field. The concentrating effect is determined by the smallest cross-section of the membrane. In a flat membrane, such as those of the prior art, a tradeoff must be made between high electroelution recovery efficiency and concentrating effect. According to the present invention, the use of a membrane having at one plane a relatively high cross-section which diminishes to a point or apex at a different plane electrically downfield advantageously mitigates any substantial trade-off.

The present apparatus also provides for the physical isolation of the gel slice, from which the biological sample is to be extracted, and the concentrating area. This dramatically reduces contaminants from fragments of gel. The concentrating area is also advantageously freed from perturbing solid or gelatinous masses. Further, this reduces the volume from which the sample is ultimately removed.

The present invention further includes a method for electrophoretically extracting biomolecules using the apparatus of the present invention. According to the present invention, the desired sample is eluted from gel slices containing the biological sample and concentrated. These gel slices are cut from a preparatory electrophoretic separation gel. Electrophoretic elution can be carried out quickly and efficiently by increasing the effective electroelution cross-sectional area of the collection semi-permeable membrane. As electrophoresis proceeds, the sample of interest is focused into the apex and becomes concentrated into a reduce volume.

Advantageously, the present apparatus can be utilized with available electrophoresis equipment. Standard buffers, buffer tanks, electrical power sources, and electrodes conventionally used in electrophoretic gel separation may be directly utilized with the present invention. The frame accordingly has an outer dimension that allows it to fit in a standard horizontal electrophoretic device's buffer tank such that the apex of the collecting membrane is closest to the positive electrode of the electrophoretic device, and the holding area for the gel slice closest to the negative electrode.

The present method by virtue of the present apparatus has all the advantages of the standard dialysis bag electroelution technique, especially the ability to extract large biomolecules, without many of the disadvantages such as the need for excessive care in the manual manipulation for creating, sealing, and positioning an amorphous bag, containing the gel slice and buffer. Further, the present method reduces both the total volume and the impurities from gel fragmentation of the gel slice.

Accordingly, it is a principal object of the present invention to provide a concentrating electroelution apparatus that allows biological samples to be advantageously extracted from separation gels.

It is another object of the present invention to provide an electroelution apparatus which carries out the extraction and concentration of the sample more quickly and completely than with prior art methods and/or apparatuses.

It is a further object of the present invention to provide a method and an apparatus that can be used with pre-existing electrophoresis equipment, such as horizontal or submarine electrophoresis devices, within their normal operating parameters.

It is a yet further object of the invention to provide improved elements and arrangements thereof in an apparatus for the purposes described which is inexpensive, dependable and fully effective in accomplishing its intended purposes, as well as easy to use.

These and other objects of the present invention will become readily apparent upon further review of the following description and drawings.

BRIEF DESCRIPTION OF THE DRAWINGS

FIG. 2 is a top view thereof with the membrane fitted within the frame.

FIG. 3 is a side view thereof.

FIG. 4 is a partial perspective cut out view of the frame.

Similar reference characters denote corresponding features consistently throughout the attached drawings.

DETAILED DESCRIPTION OF THE PREFERRED EMBODIMENT

Figure 1:
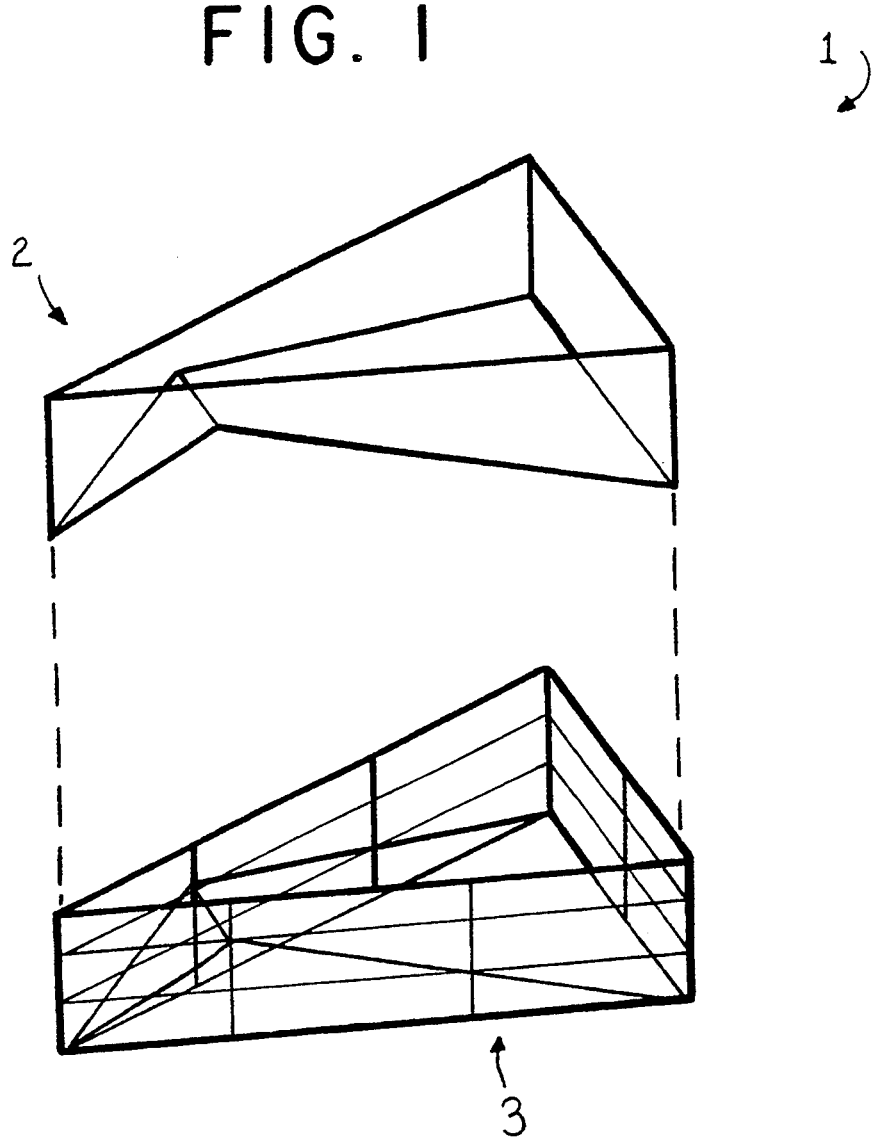
FIG. 1 is a perspective plan view of an apparatus according to a preferred embodiment of the present invention showing the frame and semi-permeable membrane.

Referring particularly to FIG. 1, the apparatus of the present invention 1 comprises a collecting membrane 2 and a supporting frame 3. As best seen in FIG. 2, the frame includes a base side 8, two converging sides 7 and 7', and a floor 6. The sides form a substantially triangular shape. As best seen in FIG. 3, the floor 6, extends from the base side 8, slopes upward, reaches a zenith 12, then more precipitously slopes downward. Apex 4 is formed at the meeting point of 7, 7', and 6.

The sides 7, 7', and 8 of the frame may be made of rigidly connected vertical posts 14 and horizontal beams 15 which allow free movement of liquid and electricity from the exterior to the interior of frame. The floor 6 may be a solid piece, or alternatively and preferably also be of plastic beam construction. More preferably, the entire frame 3 is made from plastic posts and beams, such as those of polyethylene, polypropylene, polystyrene, and acrylic. Most preferably, it is made from polypropylene and is of unitary construction.

Semi-permeable membrane 2 is shaped to snugly fit within the frame, having substantially the same dimensions as the interior of the frame. Accordingly, it comprises a bottom surface 9, a base wall section 10, and two side wall sections 11 and 11'. The meeting point of 9, 11, and 11' form an apex 5. The downward sloping surface from a zenith 12' to base wall section 10 defines a gel slice holding area 13.

A semi-permeable membrane, for the purposes of the present invention, is defined as stock sheet material having a porosity which allows water, ions, and small molecules, below a specified molecular weight cut-off, to pass through the sheet material. The membrane material must also be sufficiently transparent to electrical current to allow electrophoresis. Further, the membrane material is selected to substantially avoid binding to DNA or proteins. Preferably, less than 1% of the DNA or proteins which come in contact with the membrane surface should bind.

The semi-permeable membrane is preferably made from cellulose, cellulose acetate, or nylon having a molecular weight cutoff below the size of the molecule to be extracted. For example, a molecular weight cutoff of between about 12,000 and 14,000 daltons facilitates most DNA and protein recovery procedures. Most preferably the semi-permeable membrane is a low DNA and/or protein binding cellulose dialysis membrane. The membrane is preferably prefabricated in the desired shape.

Figure 5:
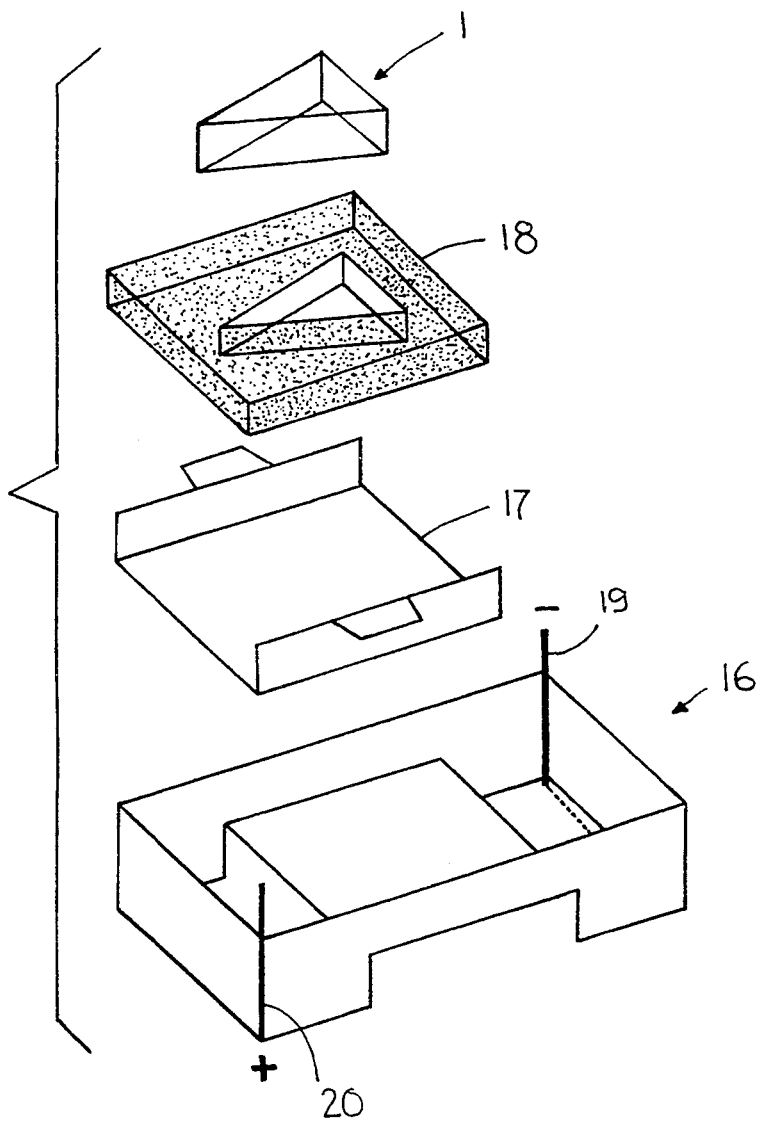
FIG. 5 is a perspective exploded view of an apparatus according to the present invention and a horizontal electrophoresis device.
Figure 6:
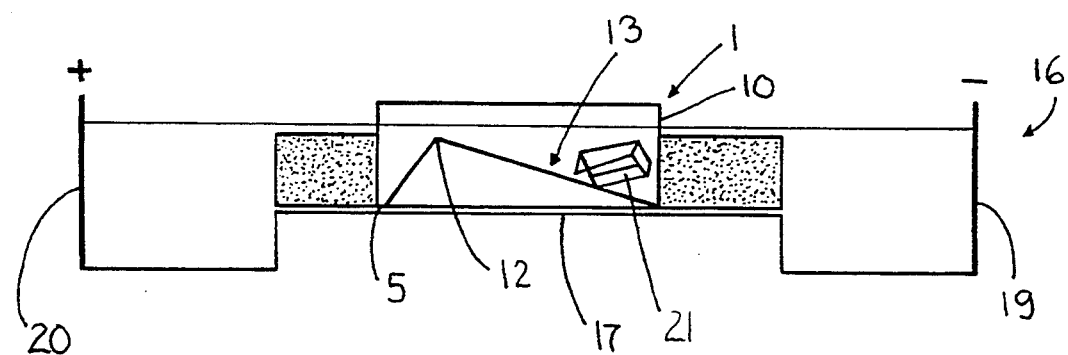
FIG. 6 is a side environmental view of an apparatus according to the present invention within a horizontal electrophoresis device.

The size of the present apparatus may be selected to fit a pre-existing horizontal electrophoresis device 16 such as shown in FIG. 5. For example, an apparatus according to the present invention sized for a standard horizontal submarine electrophoresis setup may have a membrane about 5-6 cm in axial length from the apex 5 to the base wall 10 and has a height of about 1.5 cm, with the zenith 12 located about 1 cm from the apex horizontally, and about 1 cm above the apex vertically. For double sized electrophoresis devices, the instant apparatus may be proportionally scaled up to about twice these dimensions. Similarly, the present apparatus may be scaled down to about half size. The relative proportions may also be altered, with the stipulation that the zenith must be lower than the height of the side walls, and that the horizontal distance from the apex to the zenith should be less than the horizontal distance from the base wall to the zenith.

Prior to using an apparatus according to the present invention, a preparatory electrophoretic separation is performed. Standard gels for this purpose, including the preferred agarose and polyacrylamide types may be used in either a horizontal or vertical slab. Preferred preparatory separation protocols utilize a submarine agarose gel/mini-gel or a sodium dodecyl sulfate polyacrylamide gel (SDS-PAGE) in a unidirectional electrophoresis. Markers, labels, or dyes may be used to detect the bands containing the biomolecules of interest. The concentration of the gel used is determined by the size of the molecule to be extracted and the gel material. For example, between about 0.5% and 2% agarose solution is appropriate for most DNA samples, and most preferably, about 0.5%-1.5% in a submarine agarose gel horizontal electrophoresis. Alternatively, between about 2% and 20% acrylamide solution may be used, most preferably about 5%-15% in a polyacrylamide system is appropriate for most protein samples. Any buffer appropriate for the gel system selected may be advantageously used. Typically, a Tris-acetate-EDTA (TAE) buffer is used with agarose gels. Tris buffer, with or without SDS, is likewise used with polyacrylamide gels. Once adequate separation is achieved, the bands containing the biomolecules of interest are cut from the separation gel to produce a gel slice 21. The present apparatus provides the ability to electrophoretically extract the biomolecules of interest from these gel slices.

The gel slice 21 containing the biomolecules of interest is placed into the present apparatus on the semi-permeable membrane in gel slice holding area 13. The apparatus is secured within the typically raised platform 17 of a submarine electrophoresis device buffer tank 16 by casting the apparatus 1 in a gel 18, such that the base wall is towards the negative electrode 19 and is substantially perpendicular to the direction of electrical current. The concentration and composition of the gel used in this step is not overly critical, so long as electrical current flows through the gel from the negative electrode 19 to the positive electrode 20. Advantageously, a gel having the same composition used in the separation may be used, thereby eliminating a further preparatory step. For example, an agarose gel having a concentration of about 0.5%-2% agarose may be used. The apparatus is then placed in the tank of a horizontal submarine gel electrophoresis device such that the apex 5 of the membrane is toward the positive electrode and base wall 10 is toward the negative electrode. The tank is then filled with buffer solution sufficient to cover the gel and the zenith 12 of the present apparatus. An electrical field is then applied of sufficient strength and for sufficient time to elute the sample of interest from the gel and onto the cellulose membrane at the apex of the present apparatus. A voltage of between about 25-150 V may be used, for sufficient time to allow the biological sample to completely elute out of the gel band and into the collecting area around the apex 5 of the semi-permeable membrane. Typically the time required for complete elution is less than an 30 minutes, depending on the voltage applied. Up to 99% of the molecules of interest from the sample in the original band may be transferred and concentrated in the area proximate the apex. The concentrated sample may then be removed from the apex by micropipet for use.

EXAMPLE 1

The isolation and extraction of DNA samples were performed according to a preferred embodiment of the present invention.

Step 1: DNA fragments were separated by electrophoresis in an agarose gel by submarine electrophoresis. TAE buffer was used (0.04M Tris-acetate, 0.002M EDTA, pH 8.0). A voltage of 50-100 V was applied. The concentration of the agarose gel was determined by the size of the DNA fragment desired, according to the following table:

| % Agarose | Effective range of resolution of DNA fragments (kb) |
|---|---|
| 0.5 | 30 to 1 |
| 0.7 | 12 to 0.8 |
| 1.0 | 10 to 0.5 |
| 1.2 | 7 to 0.4 |
| 1.5 | 3 to 0.2 |

Step 2: After the electrophoresis the separated bands were stained with 0.1-0.5 μg/ml ethidium bromide, and visualized by illumination with long-wave ultraviolet (UV) light. A sharp blade was used to cut out the band of interest to produce a gel slice.

Step 3: The present gel elutor and concentrator was pre-wetted and placed in the center of the gel holding area of the submarine electrophoresis device, with the apex toward the positive pole. A 0.7% agarose gel was cast to fix the concentrator in place, and the gel slice from above was placed on the membrane in the sample holding area. The submarine electrophoresis device was then filled with TAE buffer to a level such that the highest point of the floor of the present device was about 1–2 mm below the surface of the buffer.

Step 4: Electrophoresis was run at 50–100 V for 10–30 min. (the amount of time depending on the size of the DNA fragments, and the applied voltage). UV light was used to insure that all of the DNA sample had run from the gel slice, and into the concentrating apex end of the present device, before ending the electrophoresis.

Step 5: The concentrated DNA sample was pipetted out of the apex, and is ready for further applications. Up to 99% of the DNA present in the gel slice elutes into the collecting area proximate the apex of the present device. Of this, 95–98% may be recovered.

EXAMPLE 2

Proteins were isolated and extracted in the same manner as the DNA samples described in Example 1, with the following changes.

In Step 1, the gel used was an acrylamide gel, and the buffer used was from 0.125M to 0.375M Tris buffer, with or without 0.1% SDS. The concentration of acrylamide in the gel was selected according to the following table:

| % Acrylamide | Effective range of resolution of Proteins (kd) |
| --- | --- |
| 5 | 60 to 200 |
| 10 | 16 to 70 |
| 15 | 12 to 45 |

In Step 2, the desired protein band was stained and cut.

In Step 3, Tris buffer, as above was used.

In Step 4, the electrophoresis was run for a longer time, and/or at a higher voltage, to elute the protein into the apex.

It is to be understood that the present invention is not limited to the sole embodiment described above, but encompasses any and all embodiments within the scope of the following claims. Particularly, the collecting portion of the semi-permeable membrane may be of any shape which narrows to substantially a point. Such shapes include cones, pyramids of any number of sides, and skewed derivatives thereof. Accordingly, the frame would be correspondingly configured to support the membrane. Also, though the present invention has been exemplified for use with horizontal type electrophoresis device, it should be understood that the present invention encompasses embodiments adapted to be used with vertical devices, such as tube or column type electrophoresis equipment.

I claim:

1. An apparatus for the elution and concentration of biological molecules in an electrophoresis device which includes a tank, a positive electrode placed to one side along the bottom of said tank, and a negative electrode, said apparatus comprising:
    a semi-permeable membrane having a first section of continuously decreasing cross-section terminating in an apex and a contiguous second section for holding a gel slice containing biological molecules; and
    a frame sized to support said semi-permeable membrane, said frame having a first section of continuously decreasing cross-section terminating in an apex, and a contiguous second section; whereby
    when the gel slice containing the biological molecules is placed in said second section of said membrane with the apparatus secured in a tank of an electrophoresis device such that said gel slice is proximate the negative electrode of said electrophoresis device and said apex of said membrane is proximate the positive electrode of said electrophoresis device, and current is applied between the electrodes, said biological molecules are eluted out of said gel slice onto said membrane and concentrated towards said apex of said membrane.

2. The apparatus according to claim 1, wherein said frame comprises: a base side, two converging sides, and a floor,
    said base side and said converging sides form a substantially triangular shape; and
    said floor extends from said base wall, slopes upward to reach a zenith, then downward.

3. The apparatus according to claim 2, wherein said frame is constructed of a plastic selected from the group consisting of polyethylene, polypropylene, and acrylic plastics.

4. The apparatus according to claim 2, wherein said semi-permeable membrane is a cellulose membrane, and said biological molecules are selected from DNA fragments and proteins.

5. The apparatus according to claim 4, wherein said cellulose membrane is a cellulose dialysis membrane having a molecular pore size of less than the size of the biological molecule to be extracted.

6. A method for extracting biological molecules from a separation gel through electroelution comprising:
    a) cutting a band containing biological molecules of interest from a separation gel to produce a gel slice;
    b) casting a gel around the frame of the apparatus according to claim 1, thereby securing the frame within an electrophoresis device;
    c) placing said gel slice into said apparatus;
    d) placing said apparatus into an electrophoresis device which includes an electrophoresis tank, a positive electrode within said tank, a negative electrode within said tank, buffer solution within said tank, and a power source electrically connected to said positive electrode and said negative electrode, such that the gel slice containing the molecules of interest is close to the negative electrode, and the apex of the semi-permeable membrane is close to the positive electrode;
    e) applying an electric current by engaging said power source with sufficient voltage and for sufficient time such that the molecules of interest are substantially eluted out of said gel slice and onto the semi-permeable membrane at the area proximate the apex; and
    f) collecting concentrated biological molecules from said apparatus from the area proximate the apex by pipet.

7. The method according to claim 6, wherein said electrophoresis device is of the submarine gel horizontal electrophoresis type.

8. The method according to claim 7, wherein said gel is an agarose gel.

9. The method according to claim 8, wherein said agarose gel is cast from between about 0.5% and 2% agarose solution.

* * * * *